US00PP32418P2

(12) United States Plant Patent
Vinson

(10) Patent No.: US PP32,418 P2
(45) Date of Patent: Nov. 3, 2020

(54) ***FRAGARIA* PLANT NAMED 'EVES DELIGHT 2'**

(50) Latin Name: ***Fragaria* x *ananassa***
Varietal Denomination: Eves Delight 2

(71) Applicant: Edward Vinson Ltd., Faversham (GB)

(72) Inventor: Peter Edward Vinson, Faversham (GB)

(73) Assignee: Edward Vinson Ltd., Faversham (GB)

( * ) Notice: Subject to any disclaimer, the term of this patent is extended or adjusted under 35 U.S.C. 154(b) by 0 days.

(21) Appl. No.: 16/602,781

(22) Filed: Dec. 6, 2019

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

*Primary Examiner* — Susan McCormick Ewoldt
(74) *Attorney, Agent, or Firm* — Penny J. Aguirre

(57) ABSTRACT

A new cultivar of *Fragaria* plant named 'Eves Delight 2' that is characterized by its semi-upright growth habit, its conical shaped berries that are uniformly large in size, its berries with very firm skin and firm flesh, its berries that contain very high sugars and a sweet pleasant flavor, its berries that are glossy, pale red in color and retain color throughout production, and its vigorous growth with substantial fruit yields of marketable quality fruit early in season.

2 Drawing Sheets

Botanical classification: *Fragaria* x *ananassa.*

Variety denomination 'Eves Delight 2'.

BACKGROUND OF THE INVENTION

The present invention relates to a new and distinct cultivar of *Fragaria*, botanically known as *Fragaria* x *ananassa* and will be referred to hereafter by its cultivar name, 'Eves Delight 2'. 'Eves Delight 2' is a day neutral strawberry plant primarily adapted to the climate and growing conditions of the United Kingdom and other regions of similar climate and day length.

The new cultivar was derived from an ongoing breeding program conducted by the Inventor at a farm in Faversham, Kent, United Kingdom. The objective of the breeding program was to develop a new cultivar of *Fragaria* with high fruit yields, consistent cropping, good disease tolerance, and large, uniform fruit with firm skins, low acid content, and good eating quality. 'Eves Delight 2' arose from a controlled cross made by the Inventor in 2013 between an unpatented selection from the Inventor's breeding program, designated as accession number EZ05 as the female parent and an unpatented selection from the Inventor's breeding program, designated as accession number GB96 as the male parent. 'Eves Delight 2' was selected as a single unique plant in the summer of 2014 from amongst the seedlings that resulted from the above cross.

Asexual propagation of the new cultivar was first accomplished by rooting stolons in Faversham, Kent, United Kingdom in 2014. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'Eves Delight 2' as a new and unique cultivar of *Fragaria.*

1. 'Eves Delight 2' exhibits a semi-upright growth habit.
2. 'Eves Delight 2' exhibits conical shaped berries that are uniformly large in size.
3. 'Eves Delight 2' exhibits berries with very firm skin and firm flesh.
4. 'Eves Delight 2' produces berries that contain very high sugar levels and a sweet pleasant flavor.
5. 'Eves Delight 2' exhibits berries that are glossy, pale red in color and retain its color throughout production.
6. 'Eves Delight 2' exhibits vigorous growth with substantial fruit yields of marketable quality early in season.

The female parent of 'Eves Delight 2' differs from 'Eves Delight 2' in having berries that have a darker skin, flesh and core color, a denser plant canopy and smaller fruit size. The male parent of 'Eves Delight 2' differs from 'Eves Delight 2' in having darker leaves with a greater affinity for blistering, lower fruit yield, and fruit that is shorter in length and more rounded in overall shape.

'Eves Delight 2' can most closely be compared to the cultivars 'Sweet Eve' (U.S. Plant Pat. No. 21,380) and 'Eves Delight' (U.S. Plant Pat. No. 21,381). 'Sweet Eve' is similar to 'Eves Delight 2' in having a conical berry shape and a mostly re-curved calyx position relative to the fruit. 'Sweet Eve' differs from 'Eves Delight 2' in exhibiting a lower percentage of class I fruit, a softer berry flesh that results in a shorter shelf life, and trusses that are shorter in length.

The plant vigor of 'Sweet Eve' and 'Eves Delight 2' is different in multiple ways. 'Eves Delight 2' is generally taller in height than 'Sweet Eve', has a less compact and dense canopy with a slightly larger leaf size, and petiole and petiolule lengths that are considerably longer.

The leaf shape is more elongated in 'Eves Delight 2' than in 'Sweet Eve' as the 'Eves Delight 2' leaves have a slightly greater length to width ratio. On average, 'Eves Delight 2' has more serrations per leaf than 'Sweet Eve'. The majority of leaves for 'Eves Delight 2' and 'Sweet Eve' are concave in their general curvature and while both exhibit blistering, it is far more prominent in 'Sweet Eve'. 'Eves Delight 2' leaves are generally much paler green in color, with this difference becoming more apparent as the season progresses.

Despite a considerably longer truss length in 'Eves Delight 2' than 'Sweet Eve', both varieties display their inflorescences in a similar way with the majority presented level with the plant canopy.

The average corolla and calyx size for 'Sweet Eve' is larger than 'Eves Delight 2'. Both display a petal shape of a rounded base and apex with similar, if not slightly more petals in 'Eves Delight 2'.

The average berry size of 'Eves Delight 2' is larger than that of 'Sweet Eve' with better fruit shape uniformity also observed in 'Eves Delight 2'. Both varieties exhibit conical shaped berries that are glossy. While the color of both varieties is uniformly maintained throughout the season, the fruit of 'Eves Delight 2' is considerably paler in color than 'Sweet Eve'. The number of achenes is generally greater in 'Sweet Eve' compared to 'Eves Delight 2' and the achene position differs slightly. With 'Eves Delight 2', the majority of the achenes are indented whereas with 'Sweet Eve' they are split between those that are even with the fruit surface and those that are indented. There is a white band void of achenes at the top of the berry clearly present in 'Sweet Eve' that is absent or very narrow in 'Eves Delight 2'. Both 'Eves Delight 2' and 'Sweet Eve' produce berries that are high in Brix and reasonably low in acidity.

'Eve's Delight' is similar to 'Eves Delight 2' in fruit color. 'Eve's Delight' differs from 'Eves Delight 2' in cropping later in the season, having fruit that the shape differs more between primary and secondary fruit, lower average fruit yield, and leaves that are darker green in color.

BRIEF DESCRIPTION OF THE DRAWINGS

The accompanying colored photographs illustrate the overall appearance and distinct characteristics of the new cultivar as grown on table-tops in coir bags under tunnels with polyethylene covers in Faversham, Kent, United Kingdom. The photographs were taken of plants that were fruiting in early July and planted in early March from a tip taken in early July the summer before and grown as a potted plant prior to planting and overwintered above 5° C.

The photograph in FIG. 1 provides a side view of 'Eves Delight 2' with fruit.

Figure 1:
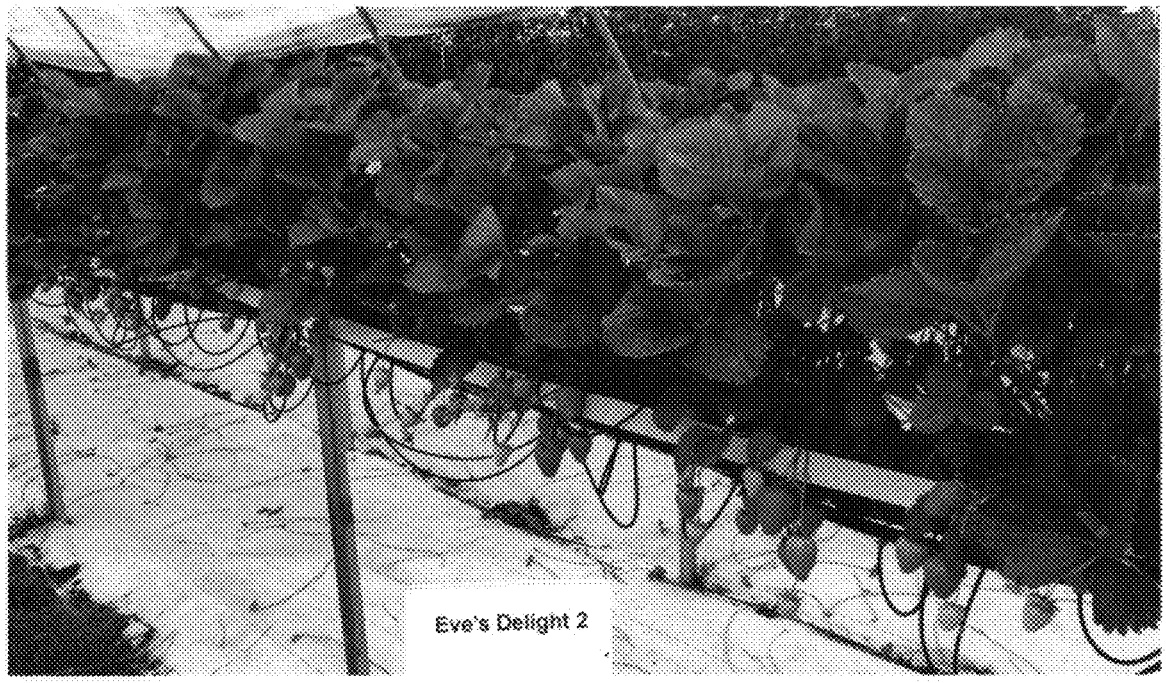
Figure 2:
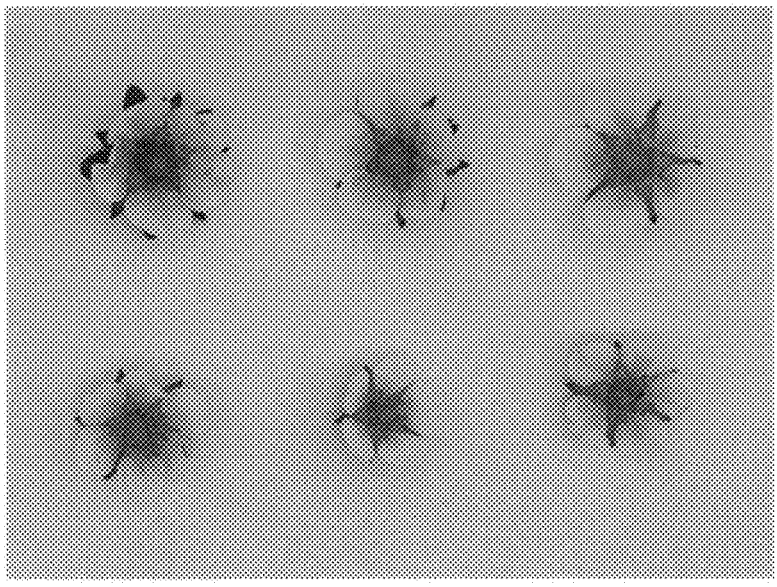
FIG. 2 provides a close-up view of the flowers of 'Eves Delight 2'.
Figure 3:
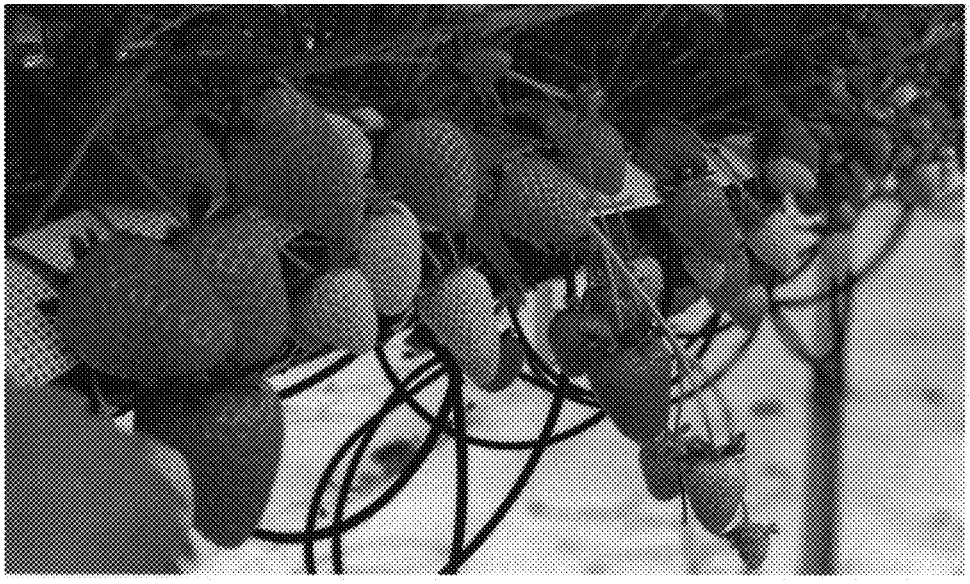
Figure 4:
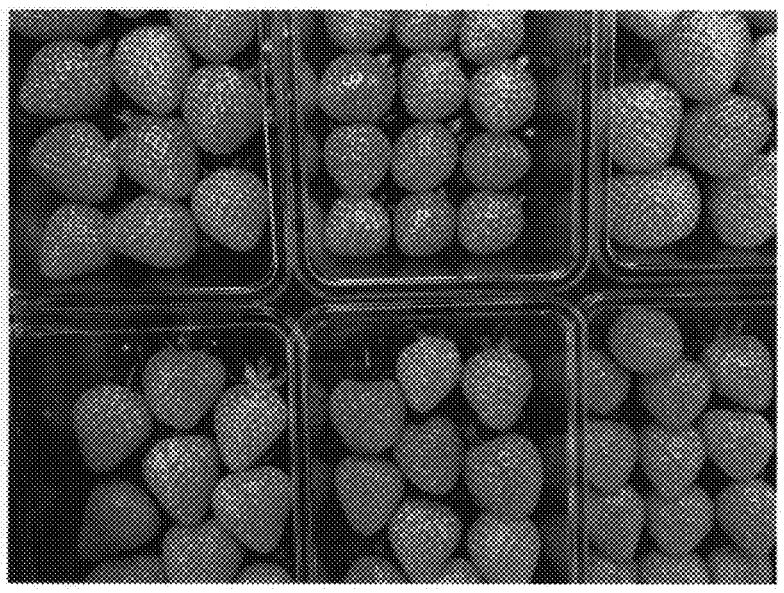

The photographs in FIG. 3 and FIG. 4 provide a close-up view of the fruit of 'Eves Delight 2'.

The colors in the photographs are as close as possible with digital photography techniques available, the color values cited in the detailed botanical description accurately describe the colors of the *Fragaria*.

DETAILED BOTANICAL DESCRIPTION

The following is a detailed description of plants of 'Eves Delight 2' as grown on table-tops, in coir bags under tunnels with polyethylene covers in Faversham, Kent, United Kingdom. The plants were fruiting in early July and planted in early March from a tip taken in early July the summer before and grown as a potted plant prior to planting and overwintered above 5° C. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Starting April and produced throughout summer in Faversham, Kent, United Kingdom.

*Plant type.*—Herbaceous fruit producing perennial.

*Plant habit.*—Semi-upright, compact with medium to sparsely dense canopy.

*Height and spread.*—Medium-large; reaches an average of 42 cm in height and 9 cm in width with an average height to width ratio of about 5:1.

*Cold hardiness.*—Not tested in areas where temperatures of less than 32° F. occur.

*Diseases.*—Tolerance to *Botryotinia cinerea* and slight susceptibility to *Podosphaera leucotricha* (powdery mildew).

*Root description.*—Fibrous, 155B in color.

*Root development.*—An average of 2 weeks to initiate roots and 5 weeks to produce a young rooted plant.

*Propagation.*—Rooting of stolons and tissue culture.

*Growth rate.*—Vigorous.

*Stem description.*—Acaulescent.

*Stolon description.*—Produced throughout the cropping season; moderate surface pubescence and anthocyanin coloration.

Foliage description:

*Leaf division.*—Compound with three leaflets.

*Leaf arrangement.*—Basal.

*Leaf attachment.*—Petiolate.

*Leaflet shape.*—Rounded.

*Mid-tier leaflet size.*—Average of 11 cm in length and 10 cm in width; an average length to width ratio of 1.1:1.

*Leaflet margins.*—Serrate to crenate, an average of 23.6 serrations per leaf.

*Leaflet base.*—Acute.

*Leaflet apex.*—Round.

*Leaflet glossiness.*—Upper surface moderate, lower surface dull.

*Leaflet aspect.*—Mostly concave.

*Leaflet interveinal blistering.*—Medium.

*Leaflet venation.*—Pinnate, coloration matches leaflet color.

*Leaflet surface.*—Upper surface glabrous, lower surface very slightly pubescent; particularly along the vein.

*Leaflet color.*—Upper surface 137C, lower surface 138B, no variegation present on either surface.

*Petiole.*—Round in shape, average of 25.3 cm in length and 4.3 mm in width, 114B in color, moderately pubescent surface with most hairs horizontal in attitude.

*Petiolules.*—Round in shape, average of 2.9 cm in length and 2.7 mm in width, moderately pubescent surface.

*Stipule.*—Average of 2 cm in length, weak anthocyanin coloration.

Flower description:

*Inflorescence.*—Truss.

*Inflorescence size.*—Average of 37.2 cm in length (average of 23 cm before branching) and 4.2 mm in width.

*Flower initiation and expression conditions.*—Temperature dependent.

*Time of flowering* (50% *of plants at first flower*).—Early season.

*Flower position relative to foliage.*—Mostly level with the leaf canopy.

*Flower diameter.*—2.9 mm.

*Flower number per truss.*—5.8.

*Flower fragrance.*—Weak.

*Calyx.*—Average of 3.04 cm in diameter, generally smaller than the corolla, mostly upwards, re-curved relative to fruit.

*Sepals.*—Average of 11.2 per flower, oblong to oblanceolate in shape with an obtuse base and an acute apex, entire margin, the adaxial color varies between 138A and 135A while the abaxial color is closest to 143A.

*Sepal position.*—Mixed arrangement relative to the fruit, most re-curving and some horizontal with fruit shoulder.

*Petals.*—5 to 7 in number, average of 1.18 cm in length and 1.17 cm in width, rounded in shape, obtuse base and apex, non-overlapping in their arrangement, entire margins, upper and lower surface glabrous and NN155C in color.

*Peduncle.*—144B in color, moderately pubescent surface with a generally horizonal hair attitude, strong in strength.

*Pedicel.*—144B in color, moderately pubescent surface with a generally upward hair attitude, strong in strength.

*Bracts.*—Observed on majority of the flower trusses from early developmental stage, which progresses into a small single leaflet as the truss matures and fruit develops, characteristics similar to leaflets.

Reproductive organs:

*Gynoecium.*—Average of 6.3 mm in width, steeply dome shaped, numerous simple pistils present with capitate shaped stigma.

*Androecium.*—Stamens; average of 18.5 per flower, shape is a cone-like tube and wider at the base, anther; oval in shape, average of 1.3 mm in length, 15A in color, pollen; moderate in quantity and close to 21B in color.

Fruit description:

*Shape.*—Predominantly conical, shape is similar for primary, secondary and tertiary fruit.

*Season of harvest.*—May through end of September in Faversham, Kent.

*Time of ripening* (50% *of plants with first ripe fruit*) .—Early.

*Type of bearing.*—Day neutral.

*Size.*—Medium to large; an average of 4.48 cm in length and 3.82 cm in width, an average length to width ratio of 1.2:1.

*Surface.*—Smooth and medium glossy.

*Calyx position.*—Mostly level with fruit and mostly re-curved.

*Attitude of calyx segments.*—Mostly re-curved with strong adherence to the fruit.

*Diameter of calyx relative to fruit diameter.*—Calyx similar in size to fruit diameter.

*Glossiness.*—Even and medium.

*External color* (*skin*).—44A and 44B, color is retained throughout the cropping season.

*Internal color* (*flesh*).—Near skin; 34A, near center; 36C.

*Evenness of color of skin.*—Very even.

*Evenness of color of flesh.*—Paler near center.

*Acidity.*—Low, total titratable acid an average of 0.71% over three seasons in trials

*Sweetness.*—High.

*Soluble solids.*—Average of 10° over three seasons in trials.

*Firmness.*—Skin is very firm (resistant to bruising), flesh is firm.

*Juiciness.*—Moderate.

*Aroma.*—Slight.

*Weight.*—Average of 22.5 g per berry and 1868 g per plant from late May to end of September over three seasons in trials.

*Number of fruit per plant.*—Average 105 from late May to end of September over three seasons in trials.

*Hollow center.*—Slight on primary, secondary and tertiary fruit, generally more prominent on primary fruit.

*Shelf life.*—Very good.

*Achene color.*—Primarily 42A with some 151D.

*Achene position.*—Majority below surface.

*Achene number.*—An average of 252 per berry.

*Band without achenes.*—Absent or very narrow.

It is claimed:

1. A new and distinct cultivar of *Fragaria* plant named 'Eves Delight 2' as herein illustrated and described.

* * * * *